(12) United States Patent
Jensen

(10) Patent No.: US 10,299,991 B2
(45) Date of Patent: May 28, 2019

(54) ROLLER COMPACTOR WITH STEAM

(71) Applicant: Freund-Vector Corporation, Marion, IA (US)

(72) Inventor: Brian K. Jensen, Cedar Rapids, IA (US)

(73) Assignee: Freund-Vector Corporation, Marion, IA (US)

( * ) Notice: Subject to any disclaimer, the term of this patent is extended or adjusted under 35 U.S.C. 154(b) by 52 days.

(21) Appl. No.: 15/715,337

(22) Filed: Sep. 26, 2017

(65) Prior Publication Data

US 2019/0091103 A1   Mar. 28, 2019

(51) Int. Cl.
*B30B 11/18*   (2006.01)
*B30B 15/30*   (2006.01)
*A61K 9/16*    (2006.01)
*A61J 3/02*    (2006.01)

(52) U.S. Cl.
CPC .............. *A61J 3/02* (2013.01); *A61K 9/1682* (2013.01); *B30B 11/18* (2013.01); *B30B 15/308* (2013.01)

(58) Field of Classification Search
None
See application file for complete search history.

(56) References Cited

U.S. PATENT DOCUMENTS 7,384,256 B1   6/2008   Clark
7,534,381 B2   5/2009   Haldar et al.

FOREIGN PATENT DOCUMENTS

| JP | H06297196 A   | 10/1994 |
| JP | 2007270030 A  | 10/2007 |
| JP | 2007277098 A  | 10/2007 |
| JP | 2014205810 A  | 10/2014 |

*Primary Examiner* — Mary Lynn F Theisen
(74) *Attorney, Agent, or Firm* — McKee, Voorhees & Sease, PLC

(57) ABSTRACT

A steam or reactant system is provided for a roller compactor to provide improved compaction or functional characteristic of powdered materials, such as active pharmaceutical ingredients. The steam or reactants can be added through conduits terminating in nozzles adjacent the nip zone of the compaction rollers. The injection nozzles can be directed tangentially from the above the rollers or laterally from the sides of the rollers. In one embodiment, the moisture is in the form of steam. The resulting compacting sheet has improved compaction characteristics and reduced compression variability.

18 Claims, 3 Drawing Sheets

ROLLER COMPACTOR WITH STEAM

BACKGROUND OF THE INVENTION

Roller compactors are often used for densification and dry granulation of powdered material. The roller compactor compacts the powdered or granular material between two rollers under pressure to produce uniform sheets of compacted powder, with a desired hardness and density. The compacted sheets can then be used to manufacture granules for various purposes, such as free flowing granules for automatic packaging of products, high density granules for reduced product packaged sizes, and granules for high speed tableting or encapsulation, with consistent dust-free purity and size.

In a conventional roller compactor machine, powder material from a hopper is pre-compacted with a screw feeder that delivers the powder to the rollers. The screw feeder may be tapered straight, helical, or a combination tapered and straight screw, as described in U.S. Pat. No. 7,384,256.

Some types of material do not compress consistently. For example, some types of powdered active pharmaceutical ingredients (API) passed through a roller compactor product granule with varying compression results, resulting in tablets with variable characteristics due to particulate size variation, crystal morphology, reaction to heat or pressure, and/or chemical variability from differing suppliers.

Therefore, a primary objective of the present invention is the provision of an improved roller compactor which mitigates compression variability of powdered materials.

Another objective of the present invention is the provision of a roller compactor using steam treatment to enhance powdered material compression.

A further objective of the present invention is a provision of a roller compactor having steam added adjacent the nip zone to improve compaction of powdered material by the rollers.

Still another objective of the present invention is a provision of a method of producing a compressed product from powdered material using a roller compactor machine with steam.

A further objective of the present invention is the provision of an improved roller compaction machine for compacting powdered materials into sheets having consistent compression characteristics.

Another objective of the present inventions is the provision of an improved roller compaction machine which compacts powdered material which does not compact well in conventional roller compactor systems.

Yet another objective of the present invention is the provision of a compacted API product made by introducing moisture adjacent the nip zone of a roller compactor so as to minimize compression variability of the compacted product.

Yet another objective of the present invention is the provision of a compacted API product made by introducing chemicals or reactants adjacent the nip zone of a roller compactor so as to minimize compression variability of the compacted product or to complete a reaction in the raw materials.

Yet another objective of the present invention is the provision is that the where steam or other reactants are introduced the compressed sheet produced does not increase significantly in moisture content.

These and other objectives have become apparent from the following description of the invention.

SUMMARY OF THE INVENTION

A roller compactor machine is provided for compressing powdered materials, particularly pharmaceutical materials, into compressed sheets having uniform and consistent compression properties throughout the sheet. The roller compactor machine includes a hopper with a feed screw to feed the powdered material to a pair of rollers. Moisture, preferably in the form of steam from a steam source, or other reactant is introduced adjacent the nip zone or point of the rollers to enhance compression uniformity of the powdered material during compaction by the rollers. The steam is added via one or more conduits from above the nip zone, or alternatively, laterally into the nip zone.

The method of the present invention produces a compressed product from powdered material using a roller compactor machine which feeds the powdered material into a nip point between a pair of rollers, with steam or moisture or other reactant added adjacent the nip zone to minimize compression variability of the compressed product.

A compacted powdered product is made, such as from active pharmaceutical ingredients, by discharging the powdered API from a hopper to the nip zone above the pair of compaction rollers, and introducing steam, moisture or another reactant adjacent the nip zone to the powdered API so as to produce a modified API, and passing the API with modified characteristics between the compaction rollers to form a compacted product.

DETAILED DESCRIPTION OF THE PREFERRED EMBODIMENTS

Figure 1:
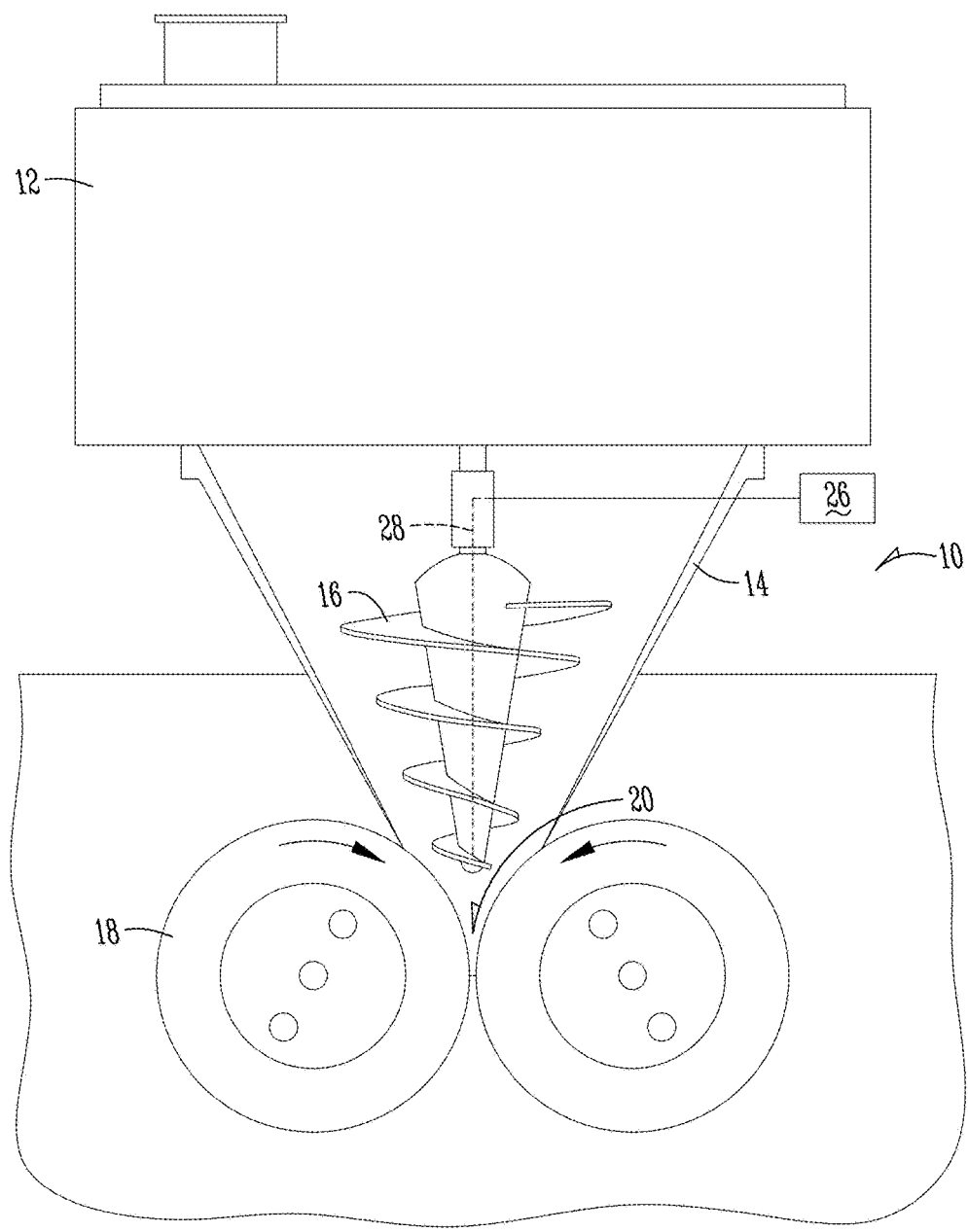
FIG. 1 is a schematic view a roller compactor machine, showing the hopper, screw, and compaction rollers.
Figure 2:
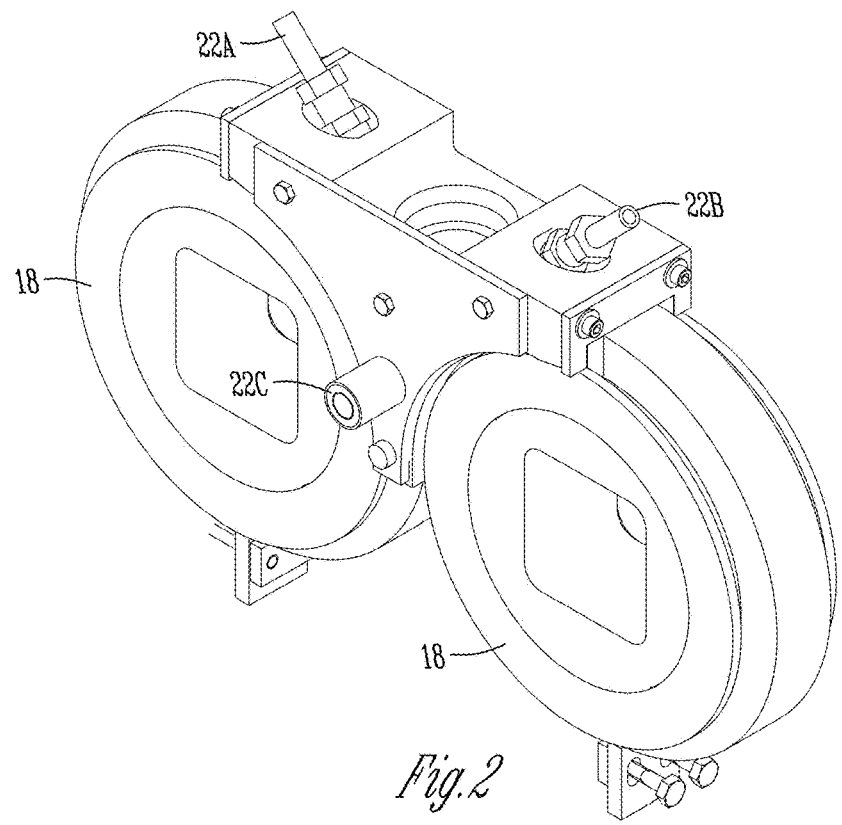
FIG. 2 is a perspective view of the rollers, with top and side steam or reactant injection options.
Figure 3:
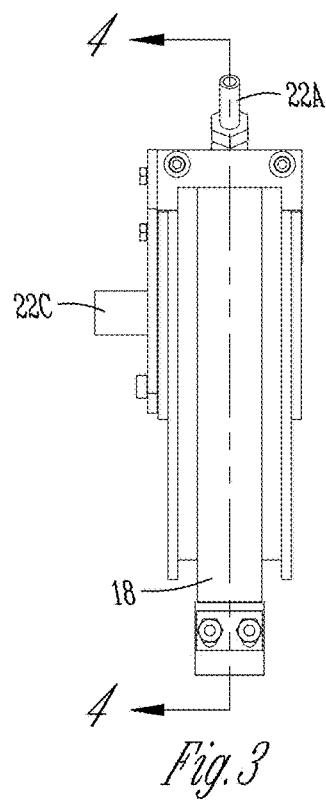
FIG. 3 is an end elevation view of the rollers and steam ports shown in FIG. 2.
Figure 4:
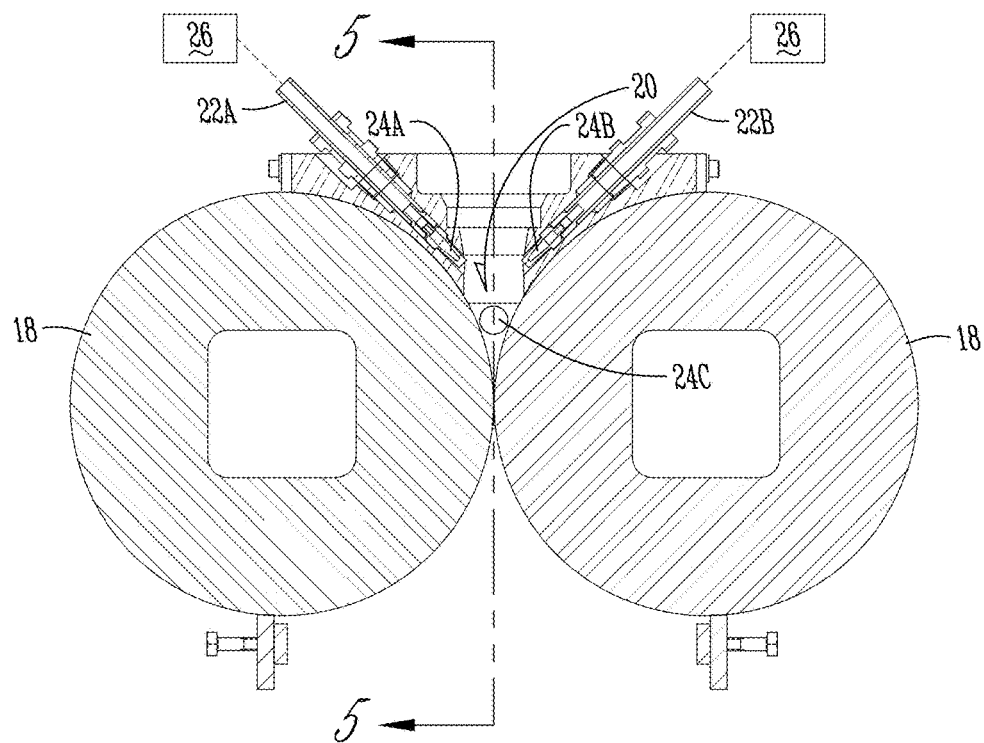
FIG. 4 is a sectional view taken along lines 4-4 of FIG. 3.
Figure 5:
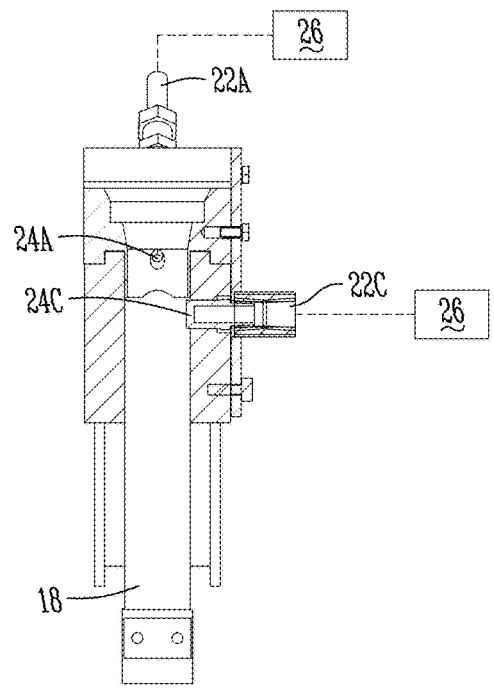
FIG. 5 is a sectional taken along lines 5-5 of FIG. 4.

As shown in FIG. 1, the roller compacter machine 10 of the present invention includes a hopper 12 for storing powdered material, such as an active pharmaceutical ingredient (API) to be compressed into sheets by the machine 10. The machine 10 also includes a discharge chute 14 with an internal screw or auger feeder 16 to direct the powder material from the hopper 12 through a pair of compaction rollers 18 which rotate in opposite directions. The chute 14 has an outlet adjacent a nip zone 20 between the rollers 18. While FIG. 1 shows the screw 16 to have a tapered profile, it is understood that the screw 16 may have other configurations such as a straight screw, or a combination straight and tapered screw, as described in applicant's U.S. Pat. No. 7,384,256.

The present invention is directed toward a steam or reactant delivery system for the roller compactor machine 10. In addition to steam, useful reactants may include, but are not limited to, acids and dilute acids, bases and dilute bases, alcohols, liquid binders, liquid polymers, and combinations of these reactants.

The steam/reactant delivery system includes one or more conduits connecting to a source of moisture to inject or deliver the moisture to an area adjacent or upstream from the nip point 20. The addition of moisture to the powder material prior to compaction by the rollers 18 provides more consistent compression of the powdered material and improves the compression characteristics of the compacted material, thereby minimizing compression variability of the compressed product. For example, mixing or injecting steam or reactants at a level of 1-50% w/w or more preferably 2-30% w/w or even more preferably 2-15% w/w creates a continuous compressed sheet of material that otherwise would be poorly compressible or incompressible or with desirable functional characteristics whereas before steam or reactant injection the compressed sheet may not have had desirable characteristics such as those of dissolution, solubility, bioavailability or other desirable characteristics. The roller compacter machine 10, in effect, acts as a mixer and single screw extruder wherein pre-mixing the powder material and moisture gives improved uniformity of content for the compressed sheet coming out of the rollers 18.

In a preferred embodiment, the desirable compression characteristics or functional characteristics are achieved by adding steam. The steam may be provided through or adjacent the nip zone 20 by one or more conduits each terminating in a nozzle. For example, conduits 22A, 22B, and 22C are shown in FIGS. 2-5. The conduits 22A, 22B are positioned above the rollers, and are directed at an angle tangential to the surface of the rollers 18, with outlets or nozzles 24A, 24B directed toward the nip point 20. Alternatively, or in addition to conduits 22A, 22B, a conduit 22C may extend transversely to the roller surfaces, parallel to the roller axes. The conduit 22C also has an outlet 24C adjacent the nip zone 20.

Thus, the steam from a source 26 may be provided from above the rollers 18, as with conduits 20A and 20B, or from the side of the rollers as with conduit 20C. These top steam injection port(s) and side steam injection port(s) function substantially the same to mix with the powder product prior to compaction so as yield an improved compressed product.

Another alternative is to provide a steam passage way 28 through the feed screw 16 to introduce the steam through an orifice at the nip zone 20. A further alternative is to introduce the steam through the rollers 18 via a rotary connection. Yet another alternative is the injection of steam through a side seal sintered plug, or other means. Yet another alternative is the extraction of steam through a side seal sintered plug, or other means. Each of the above-mentioned alternatives also hold for the injection of other gases or reactants.

While the drawings show the side injection conduit 22C as entering from the front of the rollers 18, it is understood that a side injection conduit can be provided from the back of the rollers, or from both the front and back sides of the rollers 18.

Test results show evidence of clear knurling and sharper edges through the compressed sheet, with not more than approximately 1% additional moisture content in the compressed sheet. The steam compacted API sheet can then by more easily and consistently granulated due to the improved compression characteristics.

The invention has been shown and described above with the preferred embodiments, and it is understood that many modifications, substitutions, and additions may be made which are within the intended spirit and scope of the invention. From the foregoing, it can be seen that the present invention accomplishes at least all of its stated objectives.

What is claimed is:

1. A roller compactor machine for compressing powdered pharmaceuticals, the machine having a pair of adjacent rollers defining a nip zone between the rollers and a hopper with a feed screw for feeding the powdered pharmaceuticals to the rollers, the improvement comprising:
   a source of steam; and
   a first conduit having an inlet connected to the steam source and an outlet adjacent the nip zone to introduce steam to the powdered pharmaceuticals prior to compaction by the rollers.

2. The roller compactor machine of claim 1 wherein the machine includes a side seal, and the conduit extends through the side seal.

3. The roller compactor machine of claim 1 wherein the machine includes a top seal, and the conduit extends through the top seal.

4. The roller compactor machine of claim 1 wherein the conduit extends through the feed screw.

5. The roller compactor machine of claim 1 wherein the conduit extends through one of the rollers.

6. The roller compactor machine of claim 1 further comprising a second conduit connected to the steam source and having an outlet adjacent the nip zone.

7. The roller compactor machine of claim 6 wherein the first and second conduits extend along opposite ones of the rollers.

8. A method of producing a compressed product from a powdered product using a roller compactor machine having a pair of adjacent rollers defining a nip zone between the rollers and a hopper with a feed screw for feeding the powdered pharmaceuticals to the rollers, the method comprising:
   feeding powdered material from the hopper to the rollers; and
   adding a reactant adjacent the nip zone to minimize compression variability in the compressed product.

9. The method of claim 8 wherein the reactant is steam which produces a moisture content in the compressed product of approximately 1%.

10. The method of claim 8 wherein the reactant is added through a side seal in the machine.

11. The method of claim 8 wherein the reactant is added through a top seal in the machine.

12. The method of claim 8 wherein the reactant is added through a feed screw on the machine.

13. The method of claim 8 wherein the reactant is added through one of the rollers.

14. The method of claim 8 wherein the reactant is selected from a group comprising steam, acids, bases, alcohols, liquid binders, liquid polymers, and combinations thereof.

15. A compacted API product, made by:
   supplying powdered API to a hopper;
   discharging the powdered API from the hopper to a nip zone above a pair of compaction rollers;
   introducing steam adjacent the nip zone to the powdered API to produce modified API; and
   passing the modified API between the compactor rollers so as to compact the modified API into the compacted API product.

16. The product of claim 15 wherein the modification of the API is achieved through the introduction of steam.

17. The product of claim 15 wherein the modification of the API is achieved through the introduction of a reactant other than steam.

18. The product of claim 15 wherein the compacted API product has an increased moisture content of approximately or less than 1%.

* * * * *